US00PP08518P

United States Patent [19]

Phillips

[11] Patent Number: Plant 8,518

[45] Date of Patent: Dec. 28, 1993

[54] DOGWOOD TREE 'PHILLIPS PINK NO. 1'

[76] Inventor: Walter Phillips, P.O. Box 396, Smyrna, Del. 19977

[21] Appl. No.: 772,428

[22] Filed: Oct. 7, 1991

[51] Int. Cl.[5] ..... A01H 5/00
[52] U.S. Cl. ..... Plt./53.2
[58] Field of Search ..... Plt./53.2

*Primary Examiner*—James R. Feyrer
*Assistant Examiner*—Erich Veitenheimer
*Attorney, Agent, or Firm*—Frank B. Robb

[57] ABSTRACT

A very hardy pink dogwood tree which produces many large double flower bracts which provide an almost orchid-like pink display, the tree having many such flowers as to appear as a mass of blooms.

2 Drawing Sheets

GENERAL BACKGROUND OF THE DISCLOSURE

The Dogwood Plant of my new discovery is one which was found on my farm near Frankford, Del. in an area wherein *Cornus florida* dogwood plants have been grown for some time and was thereafter transplanted to a cultivated tree and shrub bed close to my residence. I have thus had an opportunity to observe it carefully over the period of time when growth has taken place.

I have from time to time selected seedlings which I thought were of outstanding characteristics, but the instant discovery is different in many respects from any that I have found heretofore.

As stated I have a cultivated area which is devoted to dogwoods of various varieties and particularly however the *Cornus florida* variety which is so well known.

SPECIFIC DESCRIPTION OF THE INVENTION

This particular invention relates to a dogwood plant which was discovered by me as a chance seedling as before stated in a cultivated area where other dogwood varieties are grown.

It was particularly noticeable because on a windy day when I noticed the plant as it bloomed for the first time, it showed by the early color that it could have pink or red flowers. In addition, the first flower fluttered more than those on other seedlings nearby and was therefore deemed by me to be a double blossom.

After it had been transplanted from the area where it was first discovered, as time passed and the plant came into full bloom the blooms had an almost orchid-like appearance particularly emphasized by the very double nature of the blooms after the initial flower bracts reached the maximum length, and another flower developed out of the first flower center.

I am of the opinion that this plant came from the *Cornus florida* seeds because I am growing *Cornus florida* plants in the same area and have observed the same over time.

I have caused my new dogwood plant to be asexually reproduced by budding and grafting and find that it comes true in successive generations.

This new plant has been grown and observed as to its continuing attractive characteristics in the vicinity of New Brunswick, N.J., and on property controlled by me in Kent County, Del. I have determined as to those aspects which are described in detail hereafter the said plants product substantially identical characteristics in both areas where they have been tested. I note that the plant bears flowers at an early age and as it matures the limbs grow at about a 30 degree angle from the trunk. It is a narrow and erect tree thus differing from the typical *Cornus florida*. The hardiness zone 7 where the plant was discovered is in the area previously mentioned and the tree flourishes there.

The most distinguishing charactersitics of my new plant are the very double blossoms of its flower bracts and the overall pink color thereof provided by the concentration of blooms.

Detailed description is set forth in the following summary and shown in detail in the drawings wherein FIG. 1 is a view of the plant at maturity in tree form, somewhat obscured because it is growing near other dogwood trees.

FIG. 2 is illustrative of the color and shape of the leaves and flower bracts in greater detail by themselves and illustrating the very double nature thereof.

I have chosen to identify my new dogwood plant as Phillip's Pink No. 1 for purposes of identification and use in the trade. Color where referred to is as compared with Royal Horticultural Society Color Chart.

DETAILED DESCRIPTION

Figure 1:
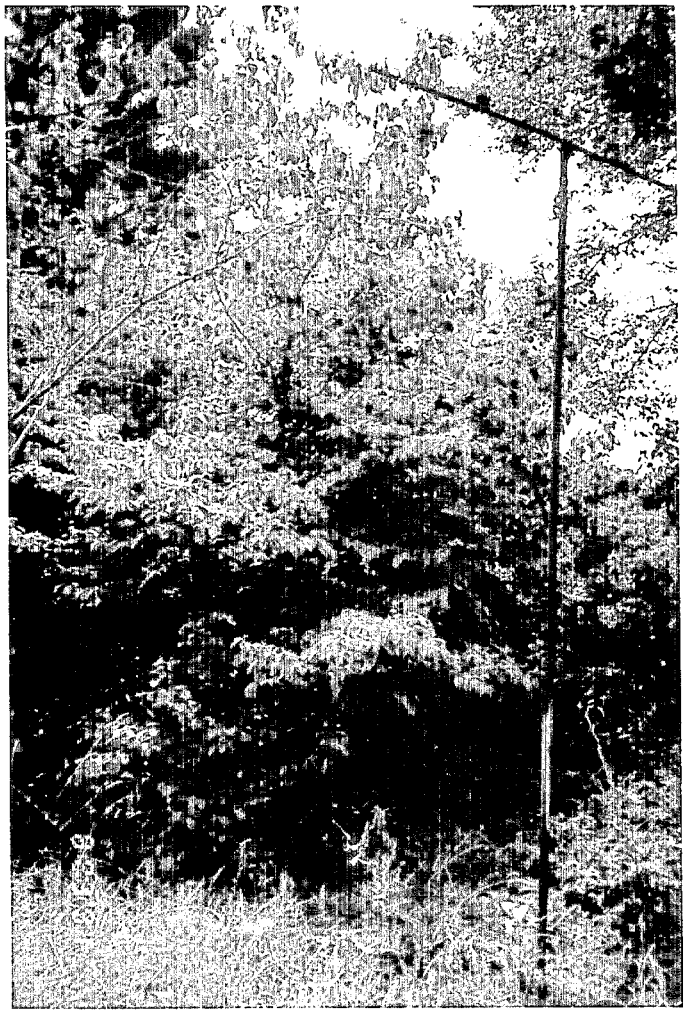
Figure 2:
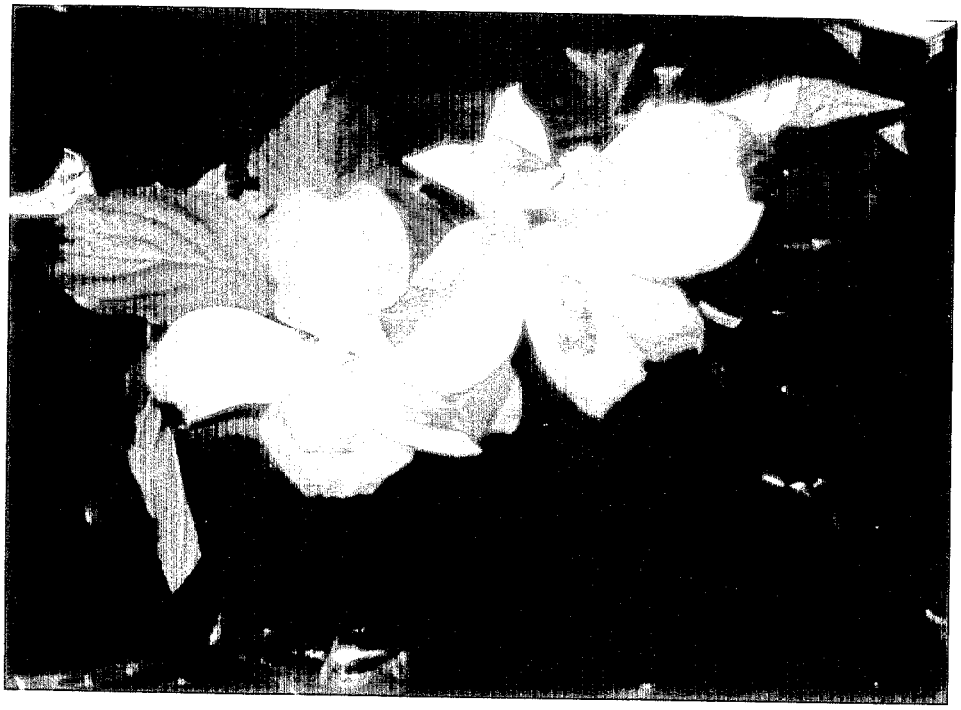

Tree: Medium, oval, spreading, dense, and hardy. Grows to a height of about 12 feet in 4 to 5 years. Spreads about 4½ to 5 feet. Grows about 5 inches in height each year to maturity. Young branches — 195 A Greyed-green group color. Old branches — 197 A Greyed-green group color. Young branches — Smooth. Lower leaf surface — 191 C Greyed-green group color. Upper leaf surface — 189 A Greyed-green group color. Vigorous, upright, round. Very productive Regular bearer

*Trunk.*—Stocky. Diameter after 5 years about 4½ to 5 inches measured 3 feet from ground, Color 199D.

*Branches.*—Slender, green color when young, gray when mature.

*Lenticels.*—Few, small.

*Leaves.*—Simple, oval, medium thickness, abundant. Length — 3½ inches to 4 inches. Width — 1¾ inches to 2 inches. Color — Dark green. Margin — Finely serrate. Petiole — Short; slender, ¼" long. Glands — None. Stipules — None.

Flower buds: Very hardy; comparable to *Cornus florida* in size, color, and shape (show slight irregularity). Fully winter hardy in Zone 7, per hardiness chart (0 degrees–10 degrees F.)

*Blooming habit.*—First bloom usually a week to ten days after other dogwoods in the area regular yearly flowering blooms last about 13 to 15 days, about 15 to 20 percent less number of blooms than Cherokee Chief and this is consistent year to year in Delaware.

*Quantity.*—Abundant.

*Size.*—Medium.

*Color.*—Light magenta (66C R.H.S. Color Chart) Royal Horticultural Society London.

*Stamens.*—Only has three to each flower.

*Bracts.*—Has four initially. After initial flower bracts are to length, then another flower will develop out of the first flower center. There is no fragrance of flowers nor is there any fruit observed.

I claim:

1. A new and distinct variety of Dogwood Plant substantially as shown and described herein, characterized particularly as to novelty by the very double form of its flower bracts, with pink overall coloration providing an orchid-like appearance, and the relatively late period of blooming as compared with other dogwood plants in the same area.

* * * * *